United States Patent
Noh et al.

(10) Patent No.: US 11,540,779 B2
(45) Date of Patent: Jan. 3, 2023

(54) BIO-INFORMATION MEASURING APPARATUS AND BIO-INFORMATION MEASURING METHOD

(71) Applicant: SAMSUNG ELECTRONICS CO., LTD., Suwon-si (KR)

(72) Inventors: Seung Woo Noh, Seongnam-si (KR); Yunseo Ku, Gwacheon-si (KR); Ui Kun Kwon, Hwaseong-si (KR); Youn Ho Kim, Hwaseong-si (KR); Chang Soon Park, Chungju-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 551 days.

(21) Appl. No.: 16/044,013

(22) Filed: Jul. 24, 2018

(65) Prior Publication Data
US 2019/0200932 A1 Jul. 4, 2019

(30) Foreign Application Priority Data
Dec. 29, 2017 (KR) .................. 10-2017-0184343

(51) Int. Cl.
*A61B 5/00* (2006.01)
*A61B 5/021* (2006.01)
(Continued)

(52) U.S. Cl.
CPC ........ *A61B 5/7207* (2013.01); *A61B 5/02007* (2013.01); *A61B 5/029* (2013.01);
(Continued)

(58) Field of Classification Search
CPC .. A61B 5/00; A61B 5/02; A61B 5/021; A61B 5/024; A61B 5/029; A61B 5/02007;
(Continued)

(56) References Cited

U.S. PATENT DOCUMENTS 4,960,126 A * 10/1990 Conlon ................ A61B 5/0456
600/336
7,184,809 B1 * 2/2007 Sterling ............. A61B 5/14551
600/322
(Continued)

FOREIGN PATENT DOCUMENTS

JP          2017522953 A     8/2017
KR    1020030072511 A     9/2003
(Continued)

OTHER PUBLICATIONS

M Hickey et al. "The effect of vascular changes on the photoplethysmographic signal at different hand elevations" Physiological Measurement, vol. 36, No. 3, 2015 Total 19 pages (pp. 425-440).
(Continued)

*Primary Examiner* — Christian Jang
*Assistant Examiner* — Mitchell E Alter
(74) *Attorney, Agent, or Firm* — Sughrue Mion, PLLC (57) ABSTRACT

A bio-information measuring apparatus bio-information measuring method are provided. The bio-information measuring apparatus includes: a pulse wave obtainer configured to obtain a pulse wave signal, and a processor configured to correct a feature of the obtained pulse wave signal based on a variation in an amplitude of the obtained pulse wave signal, and to measure bio-information based on the corrected feature.

15 Claims, 7 Drawing Sheets

(51) Int. Cl.
  *A61B 5/029* (2006.01)
  *A61B 5/024* (2006.01)
  *A61B 5/02* (2006.01)
(52) U.S. Cl.
  CPC ...... *A61B 5/02116* (2013.01); *A61B 5/02416* (2013.01); *A61B 5/4821* (2013.01); *A61B 5/7278* (2013.01); *A61B 5/746* (2013.01)
(58) Field of Classification Search
  CPC ............ A61B 5/02116; A61B 5/02416; A61B 5/4821; A61B 5/7207; A61B 5/7278; A61B 5/746
  See application file for complete search history.

(56) References Cited

U.S. PATENT DOCUMENTS

| | | | |
|---|---|---|---|
| 7,890,154 B2* | 2/2011 | Baker, Jr. | A61B 5/7221 600/323 |
| 9,173,579 B2* | 11/2015 | Berkow | A61B 5/0261 |
| 9,770,210 B2* | 9/2017 | Addison | A61B 5/7221 |
| 9,924,896 B2 | 3/2018 | De Haan et al. | |
| 2006/0020216 A1 | 1/2006 | Oishi et al. | |
| 2010/0179441 A1 | 7/2010 | Kanai et al. | |
| 2010/0298652 A1 | 11/2010 | McCombie et al. | |
| 2010/0298661 A1* | 11/2010 | McCombie | A61B 5/1114 600/301 |
| 2014/0275825 A1* | 9/2014 | Lisogurski | A61B 5/0205 600/301 |
| 2015/0164339 A1* | 6/2015 | Xu | A61H 31/005 600/324 |
| 2015/0182172 A1 | 7/2015 | Shelley et al. | |
| 2015/0366492 A1 | 12/2015 | De Haan et al. | |
| 2016/0270708 A1 | 9/2016 | Tateda et al. | |
| 2017/0055860 A1 | 3/2017 | Vermeulen et al. | |
| 2017/0172431 A1 | 6/2017 | Kim et al. | |
| 2020/0321089 A1* | 10/2020 | Nakajima | G16H 50/30 |

FOREIGN PATENT DOCUMENTS

| | | |
|---|---|---|
| KR | 1020050065995 A | 6/2005 |
| KR | 1020120043189 A | 5/2012 |
| KR | 10-2017-0073051 A | 6/2017 |
| KR | 1020170092374 A | 8/2017 |

OTHER PUBLICATIONS

Michelle Hickey et al. "Investigation of peripheral photoplethysmographic morphology changes induced during a hand-elevation study" Journal of Clinical Monitoring and Computing, vol. 30, No. 5, 2016 Total 11 pages (pp. 727-736).

Mohamed Elgendi "On the analysis of fingertip photoplethysmogram signals" Current Cardiology Reviews, vol. 8, No. 1, 2012 (pp. 14-25).

Communication dated Aug. 17, 2022 by the Korean Intellectual Property Office in Korean Patent Application No. 10-2017-0184343.

* cited by examiner

BIO-INFORMATION MEASURING APPARATUS AND BIO-INFORMATION MEASURING METHOD

CROSS-REFERENCE TO RELATED APPLICATION

This application claims priority from Korean Patent Application No. 10-2017-0184343, filed on Dec. 29, 2017 in the Korean Intellectual Property Office, the entire disclosure of which is incorporated herein by reference.

BACKGROUND

1. Field

Example embodiments of the present disclosure relate to technology for measuring bio-information in a non-invasive manner, and more particularly to a bio-information measuring apparatus and bio-information measuring method.

2. Description of the Related Art

A photoplethysmography (PPG) signal may be obtained by identifying a volume of blood present in a specific body part. The PPG signal has an advantage in that cardiovascular information may be obtained more simply and economically in a non-invasive manner, such that a PPG sensor for obtaining the PPG signal may be embedded in a mobile terminal and the like to obtain a pulse wave signal.

The PPG signal has regular waveforms synchronized with heartbeats, and the PPG waveform, which is generally generated by each heartbeat, is formed by overlapping a plurality of dicrotic waves and reflected waves.

Therefore, by analyzing a shape of the PPG signal, various types of hemodynamic information may be estimated, and bio-information may be measured based on the hemodynamic information.

As the hemodynamic information is governed by a hydrodynamics equation, signal distortion may occur due to a posture change or movement of an object.

Accordingly, research is being conducted to measure bio-information accurately even when an object moves, or distortion of the PPG signal occurs.

SUMMARY

One or more example embodiments provide a bio-information measuring apparatus and method thereof.

According to an aspect of an example embodiment, there is provided a bio-information measuring apparatus including a pulse wave obtainer configured to obtain a pulse wave signal, and a processor configured to correct a feature of the obtained pulse wave signal based on a variation in an amplitude of the obtained pulse wave signal, and to measure bio-information based on the corrected feature.

The variation in the amplitude of the pulse wave signal may include a variation in a magnitude of a direct current (DC) component or an alternating current (AC) component of the pulse wave signal.

The processor may be further configured to extract one or more features from the obtained pulse wave signal, and to correct the extracted one or more features based on a degree of dependence of the extracted one or more features on a change in the amplitude of the pulse wave signal.

The bio-information measuring, wherein in response to the variation in the amplitude of the pulse wave signal exceeding a threshold value, the processor may be further configured to correct the feature by adjusting a weighted value to be applied to correct the feature of the pulse wave signal.

The processor may be configured to adjust the weighted value to be applied to the feature of the pulse wave signal based on a correlation between the variation in the amplitude of the pulse wave signal and a variation in the feature.

The processor may be further configured to exclude a pulse wave signal, of which the amplitude variation exceeds the threshold value, from the obtained pulse wave signals.

The bio-information measuring apparatus, wherein in response to excluding the pulse wave signal, the processor may be further configured to control the pulse wave obtainer to obtain a pulse wave signal.

The bio-information measuring apparatus, wherein based on a type of the corrected feature and a degree of correction, the processor may be further configured to calculate reliability of bio-information estimated from the feature of the pulse wave signal.

The processor may be further configured to calculate a frequency of the change in the amplitude of the pulse wave signal exceeding a threshold value, and to generate guide information for changing a posture for measuring bio-information or a position of a bio-information measuring apparatus based on the calculated frequency.

The bio-information measuring apparatus may further include an output interface configured to output at least one of the pulse wave signal, the feature, an alarm generated in response to the change in the amplitude of the pulse wave signal, a guide information, user feature information, and the reliability of the bio-information.

The bio-information may include at least one of blood pressure, cardiac output, systemic vascular resistance, vascular health, and depth of anesthesia.

According to an aspect of another example embodiment, there is provided a bio-information measuring method including obtaining a pulse wave signal, measuring a variation in an amplitude of the obtained pulse wave signal, correcting a feature of the obtained pulse wave signal based on the measured variation in the amplitude of the obtained pulse wave signal, and measuring bio-information based on the corrected feature.

The variation in the amplitude of the pulse wave signal may include a variation in a magnitude of a direct current (DC) component or an alternating current (AC) component of the pulse wave signal.

The correcting of the feature may include extracting one or more features from the obtained pulse wave signal, and correcting the extracted one or more features based on a degree of dependence of the extracted features on a change in the amplitude of the pulse wave signal.

The bio-information measuring method may further include determining whether the variation in the amplitude of the pulse wave signal exceeds a threshold value, wherein in response to determination that the variation in the amplitude of the pulse wave signal exceeds the threshold value, the correcting of the feature includes correcting the feature by adjusting a weighted value to be applied to correct the feature of the pulse wave signal.

The adjusting of the weighted value may include adjusting the weighted value to be applied to the feature of the pulse wave signal based on a correlation between the variation in the amplitude of the pulse wave signal and a variation in the feature.

The bio-information measuring method may further include in response to the determination that the variation in the amplitude of the pulse wave signal exceeds the threshold value, excluding a pulse wave signal, of which the amplitude variation exceeds the threshold value, from the obtained pulse wave signals, and in response to excluding the pulse wave signal, controlling the pulse wave obtainer to obtain a pulse wave signal.

The bio-information measuring method may further include calculating reliability of bio-information estimated from the features of the pulse wave signal based on a type of the corrected features and a degree of correction.

The bio-information measuring method may further include calculating frequency of change in the amplitude of the pulse wave signal exceeding a threshold value, and generating guide information for changing a posture for measuring bio-information or a position of a bio-information measuring apparatus based on the calculated frequency.

The bio-information measuring method may further include outputting at least one of the pulse wave signal, the feature, an alarm generated in response to the change in the amplitude of the pulse wave signal, a guide information, user feature information, and a reliability of the bio-information.

BRIEF DESCRIPTION OF THE DRAWINGS

The and/or other aspects will become apparent and more readily appreciated from the following description of the example embodiments, taken in conjunction with the accompanying drawings in which.

DETAILED DESCRIPTION

Hereinafter, example embodiments of the present disclosure will be described in detail with reference to the accompanying drawings. It should be noted that, in the drawings, the same reference symbols refer to same parts although illustrated in other drawings.

Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Figure 1:
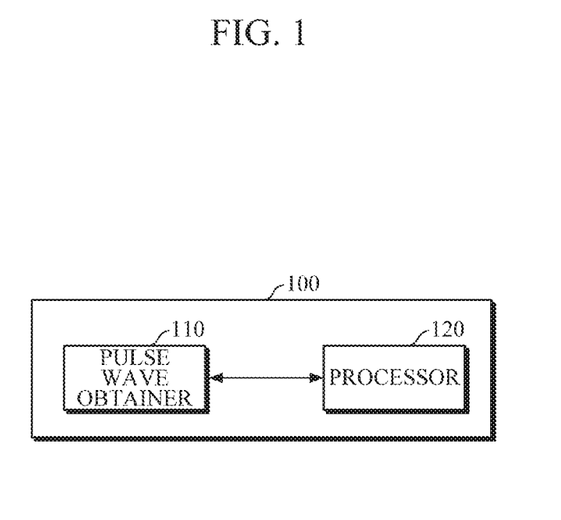
FIG. 1 is a block diagram illustrating an example of a bio-information measuring apparatus according to an example embodiment.

FIG. 1 is a block diagram illustrating an example of a bio-information measuring apparatus according to an example embodiment.

The bio-information measuring apparatus 100 may obtain a pulse wave signal from an object, and may measure bio-information of the object by analyzing a changed shape of the obtained pulse wave signal. The object may include a user using the bio-information measuring apparatus 100.

For example, the bio-information measuring apparatus 100 may extract waveforms, corresponding to one or more reflected waves and/or dicrotic waves, from the obtained pulse wave signal, and may extract features for measuring bio-information by combining the extracted waveforms.

When a user moves during measurement of a pulse wave signal, the amplitude of the pulse wave signal may change as hydrostatic pressure changes. In this case, the bio-information measuring apparatus 100 may correct features extracted from the pulse wave signal by monitoring the change in the pulse wave signal change.

For example, based on a change in a magnitude of a direct current (DC) component and/or an alternating current (AC) component of the obtained pulse wave signal, the bio-information treasuring apparatus 100 may correct the extracted features, and may measure bio-information by using the corrected features.

For example, the bio-information measuring apparatus 100 may measure, as bio-information, blood pressure by using a model for measuring bio-information such as the following Equation 1.

$$BP_{est}=a_0+a_1*f_1+a_2*f_2 \qquad \text{Equation 1}$$

Here, $BP_{est}$ denotes an estimated blood pressure value, $a_0$ denotes an offset value obtained when a user is in a stable state, $f_1$ and $f_2$ denote features extracted from a pulse wave signal, and $a_1$ and $a_2$ denote basic weighted values applied to the extracted features.

The bio-information measuring apparatus 100 may emit light onto an object, and may obtain, as a pulse wave signal, a photo plethysmography signal (hereinafter referred to as a PPG signal) by detecting light reflected or scattered from the object.

In the case of measuring blood pressure from the PPG signal, the bio-signal measuring apparatus 100 may extract features, having a high correlation with a cardiac output (CO) which indicate the volume of blood pumped by the heart in one minute, and features having a high correlation with total peripheral resistance (TPR), from the PPG signal formed by overlapping reflected waves and the dicrotic waves, may apply a weighted value to each of the features, and then may measure blood pressure by adding an offset value which is equal to a blood pressure value measured when a user is in a stable state.

For example, the bio-information measuring apparatus 100 may be mounted in a wearable device smart watch, etc.) and may obtain the PPG signal from a surface of the wrist adjacent to the radial artery, and/or may be mounted in a smart device and may obtain the PPG signal from a distal part of the body, such as fingers, toes, and the like, which has a high density of blood vessels in the body.

Upon obtaining the PPG signal, the bio-signal measuring apparatus 100 may monitor a change in the amplitude of the PPG signal, e.g., a variation in the magnitude of the AC component and/or the DC component of the PPG signal, and in response to the variation in the magnitude of the AC component and the DC component of the PPG signal exceeding a predetermined threshold value, the bio-information measuring apparatus 100 may correct features used for measuring bio-information by excluding the PPG signal, or by adjusting a weight value applied to the features extracted from the PPG signal.

In this manner, the bio-information measuring apparatus 100 may calculate variation in the magnitude of the DC component and/or AC component of the pulse wave signal obtained from a user, and may correct features used for measuring bio-information by adjusting the basic weighted values $a_1$ and $a_2$ according to dependence of the change in the features $f_1$ and $f_2$ on the variation in the amplitude of the pulse wave signal, or by excluding the obtained pulse wave signal according to the variation in the amplitude of the pulse wave signal, and thereby improving accuracy in measurement of bio-information.

The bio-information measuring apparatus 100 may measure, from the pulse wave signal, bio-information which includes, for example, blood pressure, vascular age, degree of arteriosclerosis, cardiac output, systemic vascular resistance, vascular health, stress index, degree of fatigue, and depth of anesthesia.

According to an example embodiment, the bio-information measuring apparatus 100 may measures blood pressure, but bio-information to be measured by the bio-information measuring apparatus 100 is not limited thereto.

The bio-information measuring apparatus 100 may be implemented as a software module or manufactured in the form of a hardware chip to be embedded in various types of electronic devices. In this case, examples of the electronic devices may include a cellular phone, a smartphone, a tablet personal computer (PC), a laptop computer, a personal digital assistant (PDA), a portable multimedia player (PMP), a navigation, an MP3 player, a digital camera, a wearable device, and the like. However, the electronic device is not limited to the above examples, and may include various devices.

Referring to FIG. 1, the bio-information measuring apparatus 100 may chide a pulse wave obtainer 110 and a processor 120.

The pulse wave obtainer 110 may obtain a pulse wave signal from an object.

For example, the pulse wave obtainer 110 may include a pulse wave sensor, and may obtain a pulse wave signal from the pulse wave sensor which interfaces with the object. In this case, the pulse wave sensor may include a light source which emits light onto the object, and a detector which detects light emitted by the light source and scattered or reflected from body tissues of the object, such as the skin surface, blood vessels, and the like.

The light source may include a light emitting diode (LED), a laser diode (LD), a fluorescent body, and the like. In the case where one or more light sources are provided, each of the light sources may emit light of different wavelengths.

The detector may include one or more photo diodes, photo transistors (PTr), image sensors (e.g., complementary metal-oxide semiconductor (CMOS) image sensor), and the like. In the case where one or more detectors are provided, light sources may be disposed at different distances from each of the detectors. Here, the pulse wave signal may be the PPG signal, but is not limited thereto.

The pulse wave obtainer 110 may communicate with an external device to receive a pulse wave signal of a user from the external device. For example, the pulse wave obtainer 110 may receive pulse wave data of a user from the external device by using Bluetooth communication, Bluetooth low energy (BLE) communication, near field communication (NFC), wireless local area network (WLAN) communication, Zigbee communication, infrared data association (IrDA) communication, Wi-Fi Direct (WFD) communication, ultra-wideband (UWB) communication, Ant+ communication, Wi-Fi communication, radio frequency identification (RFID) communication, and the like.

Further, examples of the external device may include a cellular phone, a smartphone, a tablet PC, a laptop computer, a personal digital assistant (PDA), a portable multimedia player (PMP), a navigation, an MP3 player, a digital camera, a wearable device, and the like. However, the external device is not limited thereto, and may include various devices for storing or measuring pulse wave data of a user.

Figure 2:
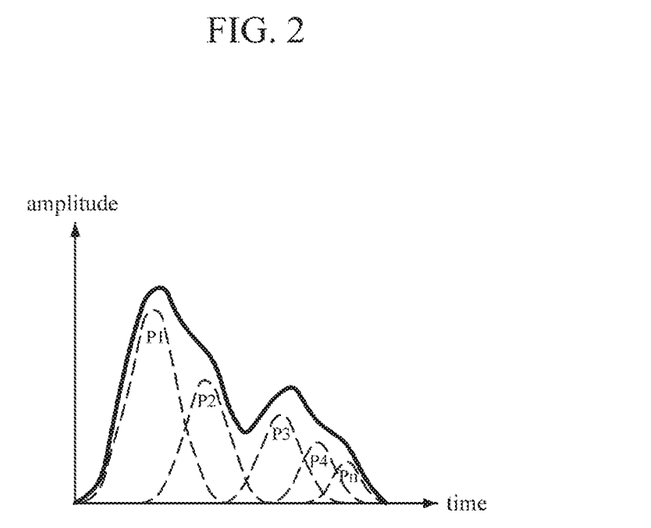
FIG. 2 is an example diagram explaining an example of extracting features from a pulse wave signal according to an example embodiment.

FIG. 2 is an example diagram explaining an example of extracting features from a pulse wave signal.

Referring to FIGS. 1 and 2, the processor 120 may extract one or more features from a pulse wave signal.

Referring to FIG. 2, a pulse wave signal (e.g., PPG signal) obtained by the pulse wave obtainer 110 may be formed by overlapping a plurality of reflected waves and dicrotic waves. In this case, the processor 120 may extract one or more reflected waves or dicrotic waves P1, P2, P3, . . . , and Pn from the pulse wave signal by analyzing the shape of the obtained pulse wave signal, and may extract features, which have a higher correlation with bio-information, from a combination of feature values (e.g., maximum value, minimum value, period, frequency, etc.) of the extracted one or more reflected waves or dicrotic waves.

Further, the processor 120 may calculate a variation in an amplitude of the obtained pulse wave.

For example, while a pulse wave signal is obtained from a user, a measurement posture of the user may be changed or a user may move, such that the amplitude of the pulse wave signal may be changed by a relative position change of an examination point with respect to a reference point.

For example, when the reference point is the position of the heart of a user, and the examination point may be a finger of the user. In the case, when a distance between the reference point and the examination point changes relative to the direction of gravity by the user's movement while the pulse wave signal is being detected, the amplitude of the pulse wave signal may change due to an effect of hydrostatic pressure.

For example, in the case where the examination point is located at a higher position than the reference point, the magnitude of the AC component of the pulse wave signal may increase, and the magnitude of the DC component of the pulse wave signal may increase because of a reduced volume of blood at the examination point.

When the examination point is located at a lower position than the reference point, the magnitude of the AC component of the pulse wave signal may decrease, and the magnitude of the DC component of the pulse wave signal may decrease with an increased volume of blood at the point to be examined.

As described above, when the pulse wave signal is obtained, a posture change or movement of a user, particularly a change in the examination point relative to the direction of gravity with respect to the reference point, may cause the amplitude of the pulse wave signal to change based on change of the effect of hydrostatic pressure, and the change in the amplitude of the pulse wave signal, which is caused by a posture change or movement of a user, may be a factor in reducing accuracy of measurement of bio-information.

Accordingly, by analyzing the shape of the pulse wave signal, the processor 120 may calculate a change in the amplitude of the pulse wave signal which is caused by the movement of a user.

Figure 3A:
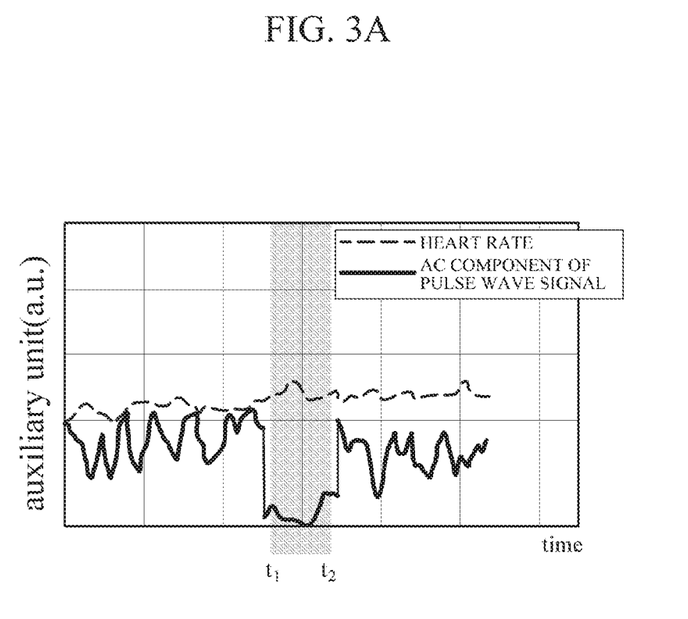
FIG. 3A is an example diagram explaining a change in an amplitude of a pulse wave signal according to an example embodiment.

FIG. 3A is an exemplary diagram illustrating a change in an amplitude of a pulse wave signal.

FIG. 3A illustrates an AC component of a PPG signal and a heart rate of a user when the user is in stable state without movement, and a change in the magnitude of the AC component of the PPG signal which is caused by movement of a user during a time period from $t_1$ to $t_2$.

In FIG. 3A, the change in the magnitude of the AC component of the PPG signal, which occurs during the time period of $t_1$ to $t_2$, is caused when a user moves while the PPG signal is continuously measured, and an examination point which is, for example, a finger is moved to a lower position than the position of the heart which is a reference point, in which case the magnitude of the AC component of the PPG signal significantly decreases. As described above, a user's movement or posture change during measurement of the pulse wave signal may cause a significant change in the AC component of the pulse wave signal, and the processor 120 may detect a change in the magnitude of the AC component of the pulse wave signal, and may calculate a variation therein.

According to an example embodiment, features, extracted from the pulse wave signal, may be corrected based on the change in the AC component of the pulse wave signal, which is caused by a user's movement or posture change during measurement of the pulse wave signal. However, example embodiments are not limited thereto, and features, extracted from the pulse wave signal, may be corrected based on a change in, for example, the DC component of the pulse wave signal.

The processor 120 may correct features for measuring bio-information based on a variation in the amplitude of the pulse wave signal.

For example, the processor 120 may compare a variation in the amplitude of the pulse wave signal with a predetermined threshold value. Upon comparison, in response to the variation in the amplitude of the pulse wave signal exceeding the predetermined threshold value, the processor 120 may correct features for measuring bio-information by adjusting a weighted value to be applied to correct features of the pulse wave signal.

For example, the processor 120 may correct features according to dependence of the features on the change in the amplitude of the pulse wave signal.

For example, based on the dependence of the features on the change in the amplitude of the pulse wave signal, the processor 120 may adjust a basic weighted value, applied to features which change more sensitively in response to the change in the amplitude of the pulse wave signal, to be lowered, and may adjust a basic weighted value, applied to features which change less sensitively in response to the change in the amplitude of the pulse wave signal, to be increased.

That is, the processor 120 may correct features for measuring bio-information by adjusting a weighted value to be applied to correct the extracted features according to how sensitively a features changes in response to a change in the amplitude of the pulse wave signal.

Further, when determining a weighted value to be applied to correct the features of the pulse wave signal, the processor 120 may adjust a weighted value to be applied to the features of the pulse wave signal by using a correlation model which is pre-generated based on a correlation between the variation in the amplitude of the pulse wave signal and a variation in the features.

In this case, the processor 120 may use a correlation model which is pre-generated by machine learning based on a correlation between the variation in the amplitude of the pulse wave signal and the variation in the features, and may also receive the correlation model from an external device.

As described above, even when the amplitude of the pulse wave signal is changed by a change in a user's posture, the processor 120 may more accurately measure bio-information by adjusting a weighted value applied to the features according to the change in the amplitude of the pulse wave signal.

In another example, the processor 120 may compare the variation in the amplitude of the pulse wave signal with a predetermined threshold value, and upon comparison, in response to the variation in the amplitude of the pulse wave signal exceeding the predetermined threshold value, the processor 120 may determine that the obtained pulse wave signal is less accurate, and may exclude the pulse wave signal.

For example, in the case where a plurality of pulse wave signals are obtained for measuring bio-information, the processor 120 may exclude a pulse wave signal, of which the amplitude variation exceeds a predetermined threshold value, from the obtained pulse wave signals, and may extract features of only the pulse wave signals, of which the amplitude variation does not exceed the predetermined threshold value.

In this manner, by excluding a pulse wave signal of which the amplitude variation exceeds a predetermined threshold value, from the plurality of pulse wave signals, and by extracting features of only the pulse wave signals of which the amplitude variation is within the predetermined threshold value, the processor 120 may improve accuracy of measurement of the bio-signal.

In addition, upon excluding the pulse wave signal, the processor 120 may control the pulse wave obtainer 110 to re-obtain a pulse wave signal.

For example, in the case where a plurality of pulse wave signals are required for measuring bio-information, the processor 120 may obtain new pulse wave signals, the number of which may correspond to the number of excluded pulse wave signals.

However, the processor 120 is not limited thereto, and when measuring bio-information continuously by using successively obtained pulse wave signals, the processor 120 may exclude a pulse wave signal of which the amplitude variation exceeds a predetermined threshold value, and may generate warning information. After generating the warning information, the processor 120 may control the pulse wave obtainer 110 to newly obtain a pulse wave signal. In this case, the warning information may be an alarm which notifies excluding of the pulse wave signal, and stopping of continuous measurement of bio-information.

Further, the processor 120 may directly obtain a pulse wave signal by controlling the pulse wave obtainer 110. However, the processor 120 is not limited thereto, and may obtain a pulse wave signal from an external apparatus for measuring a pulse wave signal through wired or wireless communications.

Figure 3B:
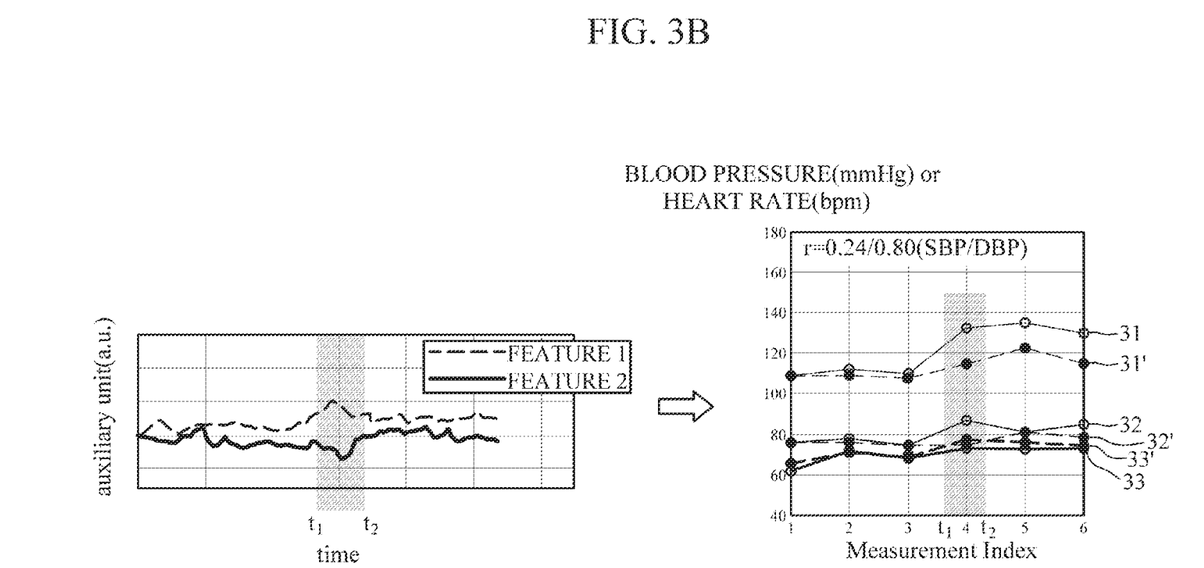
FIG. 3B is a diagram illustrating an example of measuring bio-information from the pulse wave signal of FIG. 3A.
Figure 3C:
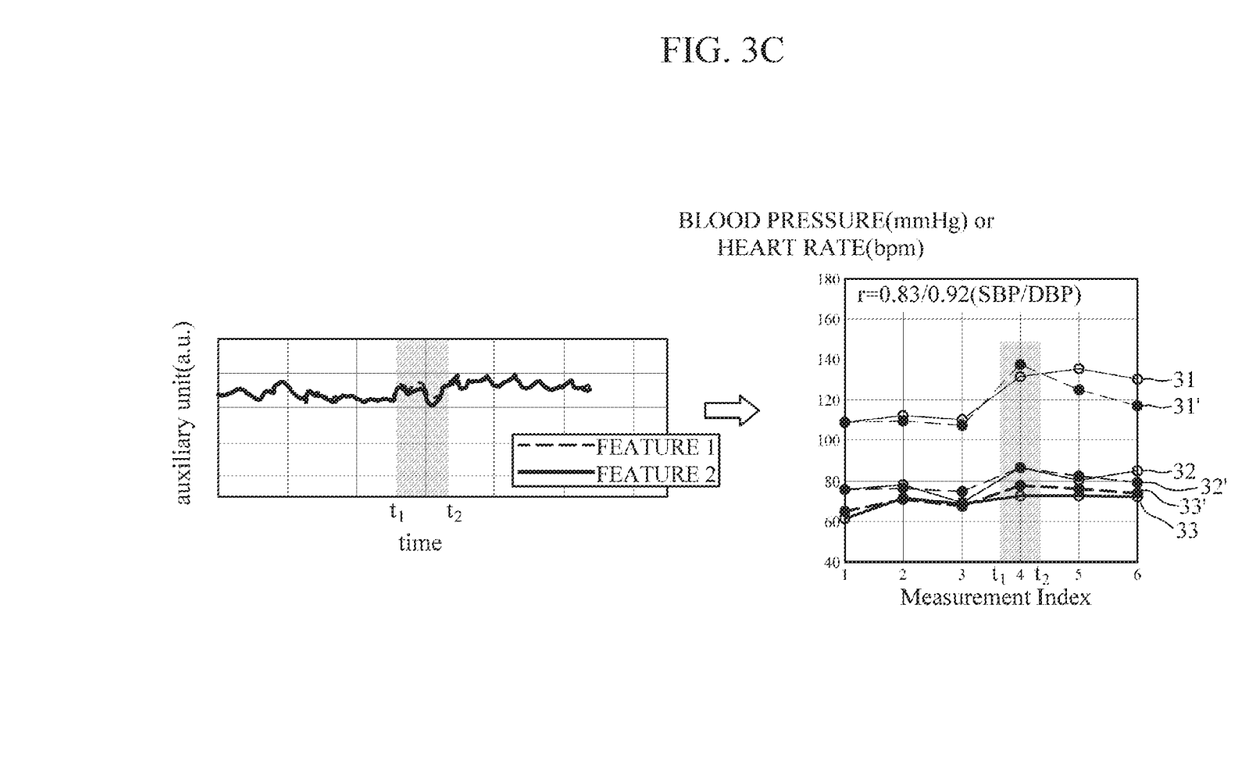
FIG. 3C is a diagram illustrating an example of measuring bio-information by correcting features based on a variation of a magnitude of an alternating current (AC) component of the pulse wave signal of FIG. 3A.

FIG. 3B is a diagram illustrating an example of measuring bio-information from the pulse wave signal of FIG. 3A, and FIG. 3C is a diagram illustrating an example of measuring bio-information by correcting features based on a variation of a magnitude of an AC component of a pulse wave signal of FIG. 3A.

FIGS. 3B and 3C illustrate actual systolic blood pressure 31, estimated systolic blood pressure 31', actual diastolic blood pressure 32, estimated diastolic blood pressure 32', an actual heart rate 33, an estimated heart rate 33', and a correlation coefficient between actual values and estimated values of the systolic pressure and the diastolic pressure.

Referring to FIGS. 3A and 3B, where a user moves during a time period of $t_1$ to $t_2$, feature 1 more sensitively changes during the time period of $t_1$ to $t_2$ as compared to feature 2. Further, a fourth estimated systolic blood pressure 31' and the fourth estimated diastolic blood pressure 32', which is estimated based on features obtained during the time period of $t_1$ to $t_2$, is lower compared to the actual systolic blood pressure 31 and the actual diastolic blood pressure 32, and underestimated.

Referring back to FIG. 3A, it can be understood that while the increase in blood pressure due to an increased heart rate may be estimated by analyzing the shape of a PPG signal, the heart rate may less sensitively change during the time period of $t_1$ to $t_2$ when the magnitude of the AC component of the pulse wave signal significantly changes by a user's movement.

Further, referring to FIG. 3B, it can be seen that even when the feature 1 is sensitively changed by a significant change in the magnitude of the AC component of e pulse wave signal, there is a higher correlation between the actual heart rate 33 and the estimated heart rate which indicates that underestimation of blood pressure due to a user's movement is not dependent only on a change in a heartbeat.

Accordingly, the processor 120 may correct features by adjusting a basic weighted value to correct a feature change caused by a user's movement.

Referring to FIGS. 3B and 3C, the processor 120 may calculate a feature 1' and a feature 2' which are respectively corrected by decreasing a basic weighted value of the feature 1 more sensitive to a change in the magnitude of the AC component of the pulse wave signal, and by increasing a basic weighted value of the feature 2 more insensitive to a change in the magnitude of the AC component of the pulse wave signal.

FIG. 3C is a diagram illustrating an estimation result of blood pressure based on the feature 1' and the feature 2' which are corrected from the feature 1 and the feature 2.

Referring to the estimation result of FIG. 3C, it can be seen that blood pressure estimated based on the feature 1' and the feature 2', which are corrected from the feature 1 and the feature 2 based on the change in the amplitude of the pulse wave signal, shows a correlation coefficient of the systolic blood pressure (SBP) increasing from 0.24 to 0.83 and a correlation coefficient of the diastolic blood pressure (DBP) increasing from 0.80 to 0.92 when compared to those before the correction of features, such that blood pressure may be estimated more accurately from the pulse wave signal.

As described above, by adaptively adjusting a basic weighted value applied to the extracted features according to a change in the amplitude of the pulse wave signal, the processor 120 may correct the features, and by measuring bio-information using the corrected features, the processor 120 may measure bio-information more accurately even when a user moves.

The processor 120 may calculate reliability of bio-information, which is estimated from the features of the pulse wave signal, based on the types of the corrected features and a degree of correction.

For example, it is assumed that between the feature 1 and the feature 2 which are extracted from the pulse wave signal, the feature 1 has a higher correlation with bio-information to be measured than the feature 2.

In the case where the feature 1 is changed more sensitively than feature 2 to a change in the amplitude of the pulse wave signal, the processor 120 may correct the feature 1 and the feature 2 by adjusting a weighted value applied to the feature 1 and the feature 2. In this case, by considering that accuracy of bio-information measured from the pulse wave signal may be low, the processor 120 may calculate that reliability of the measured bio-information is low.

According to an example embodiment, when the feature 1 and the feature 2 are changed more insensitively to a change in the amplitude of the pulse wave signal, the processor 120 may calculate that reliability of the measured bio-information is high.

That is, when measuring bio-information from the pulse wave signal, the processor 120 may calculate reliability of the measured bin-information based on a variation in the feature, which has a higher correlation with bio-information to be measured, among the features extracted from the pulse wave signal.

According to an example embodiment, the processor 120 may calculate reliability according to a degree of adjustment of a weighted value for correcting features. For example, in response to a degree of adjustment of a weighted value for correcting features being within 10% of the basic weighted value, the processor 120 may calculate that reliability of the measured bio-information is high, and in response to a degree of adjustment of a weighted value for correcting features exceeding 20% of the basic weighted value, the processor 120 may calculate that reliability of the measured bio-information is low.

Further, the processor 120 may adjust a calculation reference of reliability according to the types and/or purpose of use of bio-information to be measured.

For example, when a type of the measured bio-information is blood pressure, and the measured bin-information is used for medical purposes or medical examination purposes, the processor 120 may adjust the calculation reference of reliability to a higher level. For example, when correcting features by adjusting a weighted value which has a higher correlation with bio-information, the processor 120 may calculate that reliability of the measured bin-information is low, or when a degree of adjustment of a weighted value for correcting features exceeds 5% of the basic weighted value, the processor 120 may calculate that reliability of the measured bin-information is low. Based on calculating the reliability of the measured bio-information, accuracy of measurement may improve.

The processor 120 may measure bio-information by using the corrected features. For example, the processor 120 may measure bio-information by using a bio-information estimation model which is generated based on a correlation between the corrected features and bio-information to be measured.

In this case, the processor 120 may generate the bio-information estimation model by machine learning based on a correlation between the features, extracted from a pulse wave signal, and bio-information to be measured, and may also receive a pre-generated bio-information estimation model from an external device through wired or wireless communications.

The processor 120 may calculate frequency where a change in the amplitude of the pulse wave signal exceeds a threshold value, and may generate guide information for changing a posture for measuring bio-information or a position of a bio-information measuring apparatus based on the calculated frequency.

For example, the processor 120 may calculate frequency where a variation in the amplitude of the pulse wave signal exceeds a threshold value, and in response to the calculated frequency being higher than a predetermined reference frequency, or in response to the number of pulse wave signals, of which an amplitude variation exceeds a threshold value, exceeding a predetermined proportion of the number of the obtained pulse wave signals, the processor 120 may generate guide information for changing a posture for measuring bio-information or a position of a bio-information measuring apparatus.

For example, the bio-information measuring apparatus 100 may include one or more sensors, for example, acceleration sensor, gyro sensor, proximity sensor, camera, etc., which detect a relative position of the bio-information measuring apparatus 100 with respect to a user. In this case, the processor 120 may generate guide information for changing a posture for measuring bio-information or a position of a bio-information measuring apparatus based on the relative position of the bio-information measuring apparatus 100, which is obtained by a sensor, with respect to a user.

For example, the processor 120 may determine, as an examination point, the relative position of the bio-information measuring apparatus 100, which is obtained by a sensor, with respect to a user.

For example, in the case where the examination point is located at a different position from a reference point relative to the direction of gravity, the processor 120 may estimate a hydrostatic pressure condition of the estimated blood pressure based on the hydrostatic pressure effect.

In the hydrostatic pressure condition, if an examination point is located at a higher position than a reference point, hydrostatic pressure is decreased. In contrast, if an examination point is located at a lower position than a reference point, hydrostatic pressure is increased. Accordingly, the processor 120 may generate guide information for guiding a user to a measurement posture at which the reference point and the examination point are located at an equal position.

Figure 4:
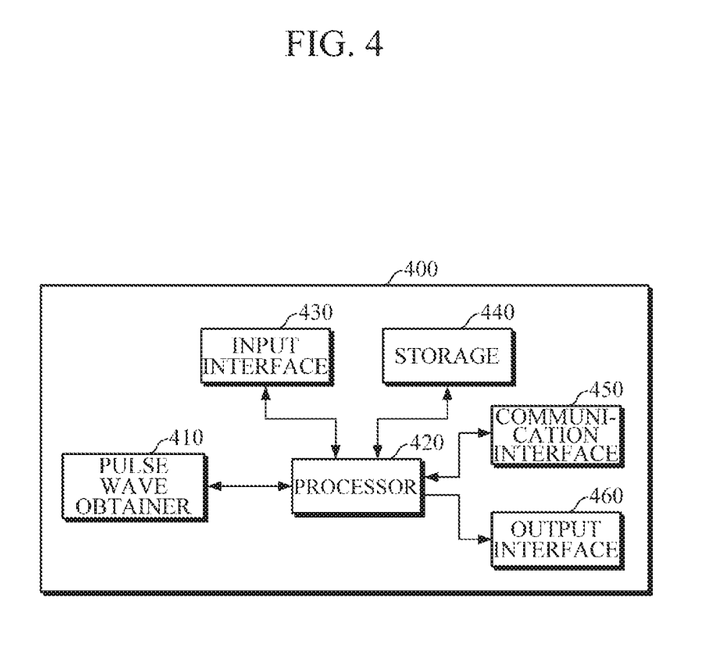
FIG. 4 is a block diagram illustrating an example of a bio-information measuring apparatus according to an example embodiment.

FIG. 4 is a block diagram illustrating an example of a bio-information measuring apparatus according to an example embodiment.

Referring to FIG. 4, the bio-information measuring apparatus 400 may include a pulse wave obtainer 410, a processor 420, an input interface 430, a storage 440, a communication interface 450, and an output interface 460. Here, the pulse wave obtainer 410 and the processor 420 generally perform the same function as the pulse wave obtainer 110 and the processor 120 described above with reference to FIG. 1.

The input interface 430 may receive input of various operation signals from a user. For example, the input interface 430 may include a keypad, a dome switch, a touch pad (static pressure/capacitance), a jog wheel, a jog switch, a hardware (H/W) button, and the like. The touch pad, which forms a layer structure with a display, may be called a touch screen.

The storage 440 may store programs or commands for operation of the bio-information measuring apparatus 400, and may store data input to and output from the bio-information measuring apparatus 400. Further, the storage 440 may store pulse wave data measured by the pulse wave obtainer 410, bio-information measured by the processor 420, and the like.

The storage 440 may include at least one storage medium of a flash memory type memory, a hard disk type memory, a multimedia card micro type memory, a card type memory (e.g., an SD memory, an XD memory, etc.) a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like. Further, the bio-information measuring apparatus 400 may operate an external storage medium, such as web storage and the like, which performs a storage function of the storage 440 on the Internet.

The communication interface 450 may perform communication with an external device. For example, the communication interface 450 may transmit, to the external device, data input from a user through the input interface 430, a user's pulse wave signal obtained by the pulse wave obtainer 110, the bio-information measured by the processor 420, location information of the bio-information measuring apparatus 400, the features extracted from the pulse wave signal, the corrected features, and the like; or may receive various data, such as a correlation model between features and weighted values, and the like, for correcting features.

In this case, the external device may be medical equipment using the measured bio-information a printer to print out results, or a display to display the measured bio-information, the extracted features and/or the corrected features. In addition, the external device may be a digital television (TV), a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 450 may communicate with an external device by using Bluetooth communication, Bluetooth low energy (BLE) communication, near field communication (NFC), WLAN communication, Zigbee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, 5G communication, and the like. However, example embodiments are not limited thereto.

The output interface 460 may output at least one of the pulse wave signal, the extracted features, the corrected features, the measured bio-information, a warning, and guide information.

For example, the output interface 460 may output at least one of the pulse wave signal, the extracted features, the corrected features, the measured bio-information, the warning, and the guide information by using at least one of an acoustic method, a visual method, and a tactile method. For example, the output interface 460 may include a display, a speaker, a vibrator, and the like.

Figure 5:
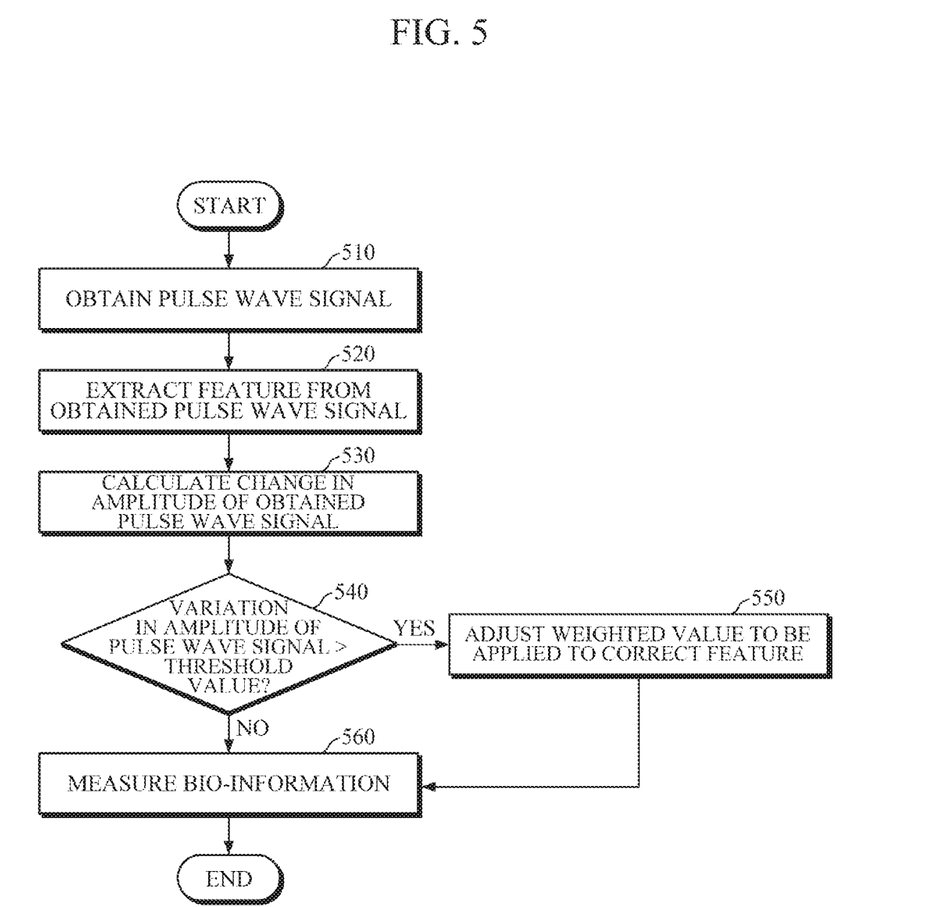
FIG. 5 is a flowchart illustrating an example of a bio-information measuring method according to an example embodiment.

FIG. 5 is a flowchart illustrating an example of a bio-information measuring method. The bio-information measuring method of FIG. 5 may be performed by the bio-information measuring apparatuses 100 and 400 illustrated in FIGS. 1 and 4.

The bio-information measuring apparatus 100 may obtain a pulse signal in 510.

For example, the bio-information measuring apparatus 100 may include a pulse wave sensor, and may obtain a pulse wave signal from the pulse wave sensor which interfaces with an object. In this case, the pulse wave sensor may include a light source which emits light onto the object, and a detector which detects light emitted by the light source and scattered or reflected from body tissues of the object, such as the skin surface, blood vessels, and the like.

The bio-information measuring apparatus 100 may emit light onto an object, and may detect a pulse wave signal by detecting light scattered or reflected from the object. However, the bio-information measuring apparatus 100 is not limited thereto, and may communicate with an external device to receive a user's pulse wave signal from the external device.

Upon measuring the pulse wave signal, the bio-information measuring apparatus 100 may extract features from the obtained pulse wave signal in 520. For example, the obtained pulse wave signal may be formed by overlapping a plurality of reflected waves and dicrotic waves.

In this case, the bio-information measuring apparatus 100 may extract one or more reflected waves or dicrotic waves P1, P2, P3, . . . , and Pn from the pulse wave signal by analyzing the shape of the obtained pulse wave signal, and may extract features, which have a higher correlation with bio-information, from a combination of feature values of the extracted one or more, reflected waves or dicrotic waves.

Then, the bio-information measuring apparatus 100 may calculate a change in an amplitude of the obtained pulse wave signal in 530.

For example, when a pulse wave signal is obtained from a user, the amplitude of the pulse wave signal may change based on a position change of an examination point with respect to a reference point.

For example, when the examination point is located at a higher position than the reference point, the magnitude of the AC component of the PPG waveform may increase, and the magnitude of the DC component of the PPG waveform may increase with a reduced volume of blood at the examination point. In contrast, when the examination point is located at a lower position than the reference point, the magnitude of the AC component of the PPG waveform may decrease, and the magnitude of the DC component of the PPG waveform may decrease with an increased volume of blood at the examination point.

Accordingly, the bio-information measuring apparatus 100 may calculate a change in the amplitude of the pulse wave signal, which is caused by a movement, by analyzing a shape of the pulse wave signal.

The bio-information measuring apparatus 100 may compare a variation in the amplitude of the pulse wave signal with a predetermined threshold value in 540.

For example, the bio-information measuring apparatus 100 may calculate a change in the amplitude of the pulse wave signal, which is caused by a movement, by analyzing a shape of the pulse wave signal, and may determine whether the calculated variation in the amplitude of the pulse wave signal exceeds the predetermined threshold value.

The bio-information measuring apparatus 100 may correct the extracted features or may measure bio-information based on the comparison between the variation in the amplitude of the pulse wave signal and the threshold value.

For example, based on the comparison, in response to the variation in the amplitude of the pulse wave signal exceeding the threshold value, the bio-information measuring apparatus 100 may adjust a weighted value to be applied to the extracted features in 550.

For example, the bio-information measuring apparatus 100 may correct the features according to dependence of the features on the change in the amplitude of the pulse wave signal.

Based on the dependence of the features on the change in the amplitude of the pulse wave signal, the bio-information measuring apparatus 100 may adjust a basic weighted value applied to features which change more sensitively to the change in the amplitude of the pulse wave signal, to be lowered, and may adjust a basic weighted value applied to features which change more insensitively to the change in the amplitude of the pulse wave signal, to be increased.

That is, the bio-information measuring apparatus 100 may correct features for measuring bio-information by adjusting a weighted value to be applied to correct the extracted features according to a change of features depending on the change in the amplitude of the pulse wave signal.

Further, when determining a weighted value to be applied to correct the features of the pulse wave signal, the bio-information measuring apparatus 100 may adjust a weighted value to be applied to the features of the pulse wave signal by using a correlation model which is pre-generated based on a correlation between the variation in the amplitude of the pulse wave signal and a variation in the features.

According to an example embodiment, upon comparing the variation in the amplitude of the pulse wave signal with a predetermined threshold value, in response to the variation in the amplitude of the pulse wave signal exceeding the predetermined threshold value, the bio-information measuring apparatus 100 may determine that the obtained pulse wave signal is less accurate, and may exclude the pulse wave signal.

For example, when a plurality of pulse wave signals are obtained for measuring bio-information, the bio-information measuring apparatus 100 may exclude a pulse wave signal, of which an amplitude variation exceeds a predetermined threshold value, from the obtained pulse wave signals, and may extract features of only the pulse wave signals, of which the amplitude variation does not exceed the predetermined threshold value.

In this manner, by excluding a pulse wave signal of which the amplitude variation exceeds a predetermined threshold value from the plurality of pulse wave signals, and by extracting features of only the pulse wave signals of which the amplitude variation is within the predetermined threshold value, the bio-information measuring apparatus 100 may improving accuracy of the measured bio-signal.

In addition, the bio-information measuring apparatus 100 may calculate reliability of bio-information, which is estimated from the features of the pulse wave signal, based on the types of the corrected features and a degree of correction.

For example, it is assumed that between feature 1 and feature 2 extracted from the pulse wave signal, the feature 1 has a higher correlation with bio-information to be measured than the feature 2.

In the case where the feature 1 changes more sensitively than the feature 2 to a change in the amplitude of the pulse wave signal, the bio-information measuring apparatus 100 may correct the feature 1 and the feature 2 by adjusting a weighted value applied to the feature 1 and the feature 2. In this case, by considering that accuracy of bio-information measured from the pulse wave signal may be low, the bio-information measuring apparatus 100 may calculate that reliability of the measured bio-information is low.

According to an example embodiment, when the feature 1 and the feature 2 change less sensitively to a change in the amplitude of the pulse wave signal, the bio-information measuring apparatus 100 may calculate that reliability of the measured bio-information is high.

That is, when measuring bio-information from the pulse wave signal, the bio-information measuring apparatus 100 may calculate reliability of the measured bio-information based on a variation in the feature, which has a higher correlation with bio-information to be measured, among the features extracted from the pulse wave signal.

According to an example embodiment, the bio-information measuring apparatus 100 may calculate reliability according to a degree of adjustment of a weighted value for correcting features. For example, in response to a degree of adjustment of a weighted value for correcting features being within 10% of the basic weighted value, the bio-information measuring apparatus 100 may calculate that reliability of the measured bio-information is high, and in response to a degree of adjustment of a weighted value for correcting features exceeding 20% of the basic weighted value, the bio-information measuring apparatus 100 may calculate that reliability of the measured bio-information is low.

Further, the bio-information measuring apparatus 100 may adjust a calculation reference of reliability according to the types and/or purpose of use of bio-information to be measured.

For example, in the case where a type of the measured bio-information is blood pressure, and the measured bio-information is used for medical purposes or medical examination purposes, the bio-information measuring apparatus 100 may adjust the calculation reference of reliability to a higher level. For example, when correcting features by adjusting a weighted value which has a higher correlation with bio-information, the bio-information measuring apparatus 100 may calculate that reliability of the measured bio-information is low, or in the case where a degree of adjustment of a weighted value for correcting features exceeds 5% of the basic weighted value, the bio-information measuring apparatus 100 may calculate that reliability of the measured bio-information is low. Based on calculating the reliability of the measured bio-information, accuracy of measurement may improve.

The bio-information measuring apparatus 100 may calculate frequency that a change in the amplitude of the pulse wave signal exceeds a threshold value, and may generate guide information for changing a posture for measuring bio-information or a position of a bio-information measuring apparatus based on the calculated frequency.

For example, the bio-information treasuring apparatus 100 may calculate frequency that a variation in the amplitude of the pulse wave signal exceeds a threshold value, and in response to the calculated frequency being higher than a predetermined reference frequency, or in response to the number of pulse wave signals of which an amplitude variation exceeds a threshold value exceeding a predetermined proportion of the number of the obtained pulse wave signals, the bio-information measuring apparatus 100 may generate guide information for changing a posture for measuring bio-information or a position of a bio-information measuring apparatus.

For example, the bio-information measuring apparatus 100 may generate guide information for changing a position of the bio-information measuring apparatus by considering a hydrostatic pressure condition. In the hydrostatic pressure condition, if an examination point is located at a higher position than a reference point, hydrostatic pressure is decreased, by contrast, if an examination point is located at a lower position than a reference point, hydrostatic pressure is increased. Accordingly, the bio-information measuring apparatus 100 may generate guide information for guiding a user to a measurement posture at which the reference point and the examination point are located at an equal position.

The bio-information measuring apparatus 100 may measure bio-information based on the features extracted from the pulse wave signal in 560.

For example, in response to the variation in the amplitude of the pulse wave signal exceeding a threshold value, the bio-information measuring apparatus 100 may measure bio-information based on the corrected features. In response to the variation in the amplitude of the pulse wave signal not exceeding the threshold value, the bio-information measuring apparatus 100 may measure bio-information based on the extracted features.

In this case, the bio-information measuring apparatus 100 may measure bio-information by using a bio-information estimation model generated based on a correlation between the extracted features and bio-information to be measured.

The bio-information measuring apparatus 100 may generate the bio-information estimation model by machine learning based on a correlation between the features, extracted from a pulse wave signal, and bio-information to be measured, and may also receive a pre-generated bio-information estimation model from an external device through wired or wireless communications.

Upon measuring the bio-information, the bio-information measuring apparatus 100 may display at least one of the obtained pulse wave signal, the extracted features, the corrected features, the measured bio-information, the warning, and the guide information.

The present disclosure can be realized as a computer-readable code written on a computer-readable recording medium. Codes and code segments needed for realizing the present disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

While one or more embodiments have been described with reference to the figures, it will be understood by those of ordinary skill in the art that various changes in form and details may be made therein without departing from the spirit and scope as defined by the following claims.

What is claimed is:

1. A bio-information measuring apparatus comprising:
   a pulse wave sensor configured to obtain a pulse wave signal;
   a processor configured to:
   extract at least two types of features of the obtained pulse wave signal, the features of the obtained pulse wave signal comprising a period and a frequency of the pulse wave signal,
   obtain an amplitude of the pulse wave signal,
   determine whether a variation in the amplitude of the pulse wave signal exceeds a threshold value,
   in response to the variation in the amplitude of the pulse wave signal exceeding the threshold value, correct the at least two types of features of the obtained pulse wave signal by adjusting weighted values to be applied to the at least two types of features of the pulse wave signal based on a degrees of dependence of the at least two types of features on the variation in an amplitude of the obtained pulse wave signal, and
   measure bio-information based on the corrected at least two types of features; and
   an output interface configured to output the measured bio-information and at least one of the pulse wave signal and the at least two types of features,
   wherein the bio-information comprises at least one of blood pressure, cardiac output, systemic vascular resistance, and depth of anesthesia.

2. The bio-information measuring apparatus of claim 1, wherein the variation in the amplitude of the pulse wave signal comprises a variation in a magnitude of a direct current (DC) component or an alternating current (AC) component of the pulse wave signal.

3. The bio-information measuring apparatus of claim 1, wherein the processor is configured to adjust the weighted value to be applied to the at least two types of features of the pulse wave signal based on a correlation between the variation in the amplitude of the pulse wave signal and a variation in each of the at least two types of features.

4. The bio-information measuring apparatus of claim 1, wherein the processor is further configured to exclude the pulse wave signal based on the variation in the amplitude of the pulse wave signal exceeding the threshold value.

5. The bio-information measuring apparatus of claim 4, wherein in response to excluding the pulse wave signal, the processor is further configured to control the pulse wave sensor to obtain another pulse wave signal.

6. The bio-information measuring apparatus of claim 1, wherein based on a type of the corrected at least two types of features and a degree of correction, the processor is further configured to determine a reliability of bio-information measured from the at least two types of features of the pulse wave signal.

7. The bio-information measuring apparatus of claim 1, wherein the processor is further configured to determine a frequency of the variation in the amplitude of the pulse wave signal exceeding the threshold value, and to generate guide information for changing a posture for measuring the bio-information or a position of the bio-information measuring apparatus based on the determined frequency.

8. The bio-information measuring apparatus of claim 1, wherein the output interface is further configured to output at least one of an alarm generated in response to the variation in the amplitude of the pulse wave signal, guide information, user feature information, and a reliability of the bio-information.

9. A bio-information measuring method comprising:
   obtaining a pulse wave signal;
   extracting at least two types of features of the obtained pulse wave signal, the features of the obtained pulse wave signal comprising a period and a frequency of the pulse wave signal;
   obtaining an amplitude of the pulse wave signal;
   measuring a variation in the amplitude of the obtained pulse wave signal;
   determining whether the variation in the amplitude of the pulse wave signal exceeds a threshold value;
   in response to determining that the variation in the amplitude of the pulse wave signal exceeds the threshold value, correcting the at least two types of features of the obtained pulse wave signal by adjusting weighted values to be applied to the at least two types of features of the pulse wave signal based on degrees of dependence of the at least two types of features on the measured variation in the amplitude of the obtained pulse wave signal;
   measuring bio-information based on the corrected at least two types of features; and
   outputting the measured bio-information and at least one of the pulse wave signal and the at least two types of features of the obtained pulse wave signal,
   wherein the bio-information comprises at least one of blood pressure, cardiac output, systemic vascular resistance, and depth of anesthesia.

10. The bio-information measuring method of claim 9, wherein the variation in the amplitude of the pulse wave signal comprises a variation in a magnitude of a direct current (DC) component or an alternating current (AC) component of the pulse wave signal.

11. The bio-information measuring method of claim 9, wherein the adjusting of the weighted value comprises adjusting the weighted value to be applied to the at least two types of features of the pulse wave signal based on a correlation between the variation in the amplitude of the pulse wave signal and a variation in each of the at least two types of features of the obtained pulse wave signal.

12. The bio-information measuring method of claim 9, further comprising:
    in response to determining that the variation in the amplitude of the pulse wave signal exceeds the threshold value, excluding the pulse wave signal; and
    in response to excluding the pulse wave signal, obtaining another pulse wave signal.

13. The bio-information measuring method of claim 9, further comprising determining a reliability of bio-information measured from the at least two types of features of the pulse wave signal based on a type of the corrected at least two types of features of the pulse wave signal and a degree of correction.

14. The bio-information measuring method of claim 9, further comprising:
    determining a frequency of change in the amplitude of the pulse wave signal exceeding the threshold value; and
    generating guide information for changing a posture for measuring the bio-information or a position of a bio-information measuring apparatus based on the determined frequency.

15. The bio-information measuring method of claim 9, further comprising outputting at least one of an alarm generated in response to the variation in the amplitude of the pulse wave signal, guide information, user feature information, and a reliability of the bio-information.

\* \* \* \* \*